US012558333B2

(12) United States Patent
Tani et al.

(10) Patent No.: US 12,558,333 B2
(45) Date of Patent: Feb. 24, 2026

(54) AGENT FOR AMELIORATING AND/OR PREVENTING SICKLE CELL DISEASE

(71) Applicants: The University of Tokyo, Tokyo (JP); NEOPHARMA JAPAN CO., LTD., Shizuoka (JP)

(72) Inventors: Kenzaburo Tani, Tokyo (JP); Yasushi Soda, Tokyo (JP); Jiyuan Liao, Tokyo (JP); Shohei Miyamoto, Tokyo (JP); Satofumi Kawata, Tokyo (JP); Motoyasu Tomioka, Tokyo (JP); Ken Kodama, Tokyo (JP)

(73) Assignees: The University of Tokyo, Tokyo (JP); NEOPHARMA JAPAN CO., LTD., Fukuroi (JP)

( * ) Notice: Subject to any disclaimer, the term of this patent is extended or adjusted under 35 U.S.C. 154(b) by 662 days.

(21) Appl. No.: 17/753,971

(22) PCT Filed: Sep. 18, 2020

(86) PCT No.: PCT/JP2020/035616
§ 371 (c)(1),
(2) Date: Mar. 18, 2022

(87) PCT Pub. No.: WO2021/054473
PCT Pub. Date: Mar. 25, 2021

(65) Prior Publication Data

US 2022/0331276 A1 Oct. 20, 2022

(30) Foreign Application Priority Data

Sep. 19, 2019 (JP) ................................ 2019-170764

(51) Int. Cl.
*A61K 31/197* (2006.01)
*A61K 33/26* (2006.01)
*A61P 7/00* (2006.01)

(52) U.S. Cl.
CPC ............ *A61K 31/197* (2013.01); *A61K 33/26* (2013.01); *A61P 7/00* (2018.01)

(58) Field of Classification Search
CPC .......... A61K 31/197; A61K 33/26; A61P 7/00
See application file for complete search history.

(56) References Cited

U.S. PATENT DOCUMENTS 6,384,076 B1 5/2002 Manion et al.
2005/0158401 A1 7/2005 Morris
2013/0108710 A1* 5/2013 Tanaka .................. A61K 33/26 514/561
2014/0288172 A1 9/2014 Tanaka et al.
2015/0037297 A1* 2/2015 Terman ................ A61K 9/5068 424/93.21
2015/0216830 A1 8/2015 Rephaeli et al.
2021/0145783 A1 5/2021 Pace et al.

FOREIGN PATENT DOCUMENTS

WO WO 00/18418 A2 4/2000
WO WO 2004/073623 A2 9/2004
WO WO 2011/145343 A1 11/2011
WO WO 2013/054755 A1 4/2013
WO WO 2015/006498 * 1/2015
WO WO 2018/204764 * 11/2018

OTHER PUBLICATIONS

Wikepedia (retrived 2025).*
Hariharan et al., "Bleeding in patients with sickle cell disease: a population-based study;" Blood Advances (Mar. 10, 2020), vol. 4, No. 5, pp. 793-802.
International Search Report mailed Oct. 27, 2020, in PCT/JP2020/035616.
Murray et al., "Global, regional, and national life expectancy, all-cause mortality, and cause-specific mortality for 249 causes of death, 1980-2015: a systematic analysis for the Global Burden of Disease Study 2015," Lancet (2016), vol. 388, pp. 1459-1544.
Murray et al., "Global, regional, and national incidence, prevalence, and years lived with disability for 310 diseases and injuries, 1990-2015: a systematic analysis for the Global Burden of Disease Study 2015," Lancet (2016), vol. 388, pp. 1545-1602.
Oseghale et al., "Conjugate prodrug AN-233 induces fetal hemoglobin expression in sickle erythroid progenitors and β-YAC transgenic mice," Blood Cells, Molecules and Diseases (2019), vol. 79, 102345, pp. 1-8.
Rephaeli et al., "Bi-functional prodrugs of 5-aminoevulinic acid and butyric acid increase erythropoiesis in anemic mice in an erythropoietin-independent manner;" European Journal of Pharmaceutical Sciences (2016), Vo. 91, pp. 91-97.
Telen et al., "Therapeutic strategies for sickle cell disease; towards a multi-agent approach," Nat. Rev. Drug Discov (Feb. 2019), vol. 18, No. 2, pp. 139-158.
Vos et al., "Global, regional, and national incidence, prevalence and years lived with disability for 301 acute and chronic diseases and injuries in 188 countries, 1990-2013: a systematic analysis for the Global Burden of Disease Study 2013," Lancet (Aug. 22, 2015), vol. 386, No. 9995, ppp. 743-800.

* cited by examiner

*Primary Examiner* — Shirley V Gembeh
(74) *Attorney, Agent, or Firm* — Birch, Stewart, Kolasch & Birch, LLP

(57) ABSTRACT

An agent for ameliorating and/or preventing sickle cell disease, includes 5-aminolevulinic acid (ALA) or a derivative thereof or a salt thereof. The agent is useful for amelioration and/or prevention of sickle cell disease. The agent may include one or more kinds of metal-including compounds. The metal in the metal-including compound can be any of several different metals, including iron, magnesium, zinc, nickel, vanadium, copper, chromium, molybdenum, or cobalt.

15 Claims, 7 Drawing Sheets

AGENT FOR AMELIORATING AND/OR PREVENTING SICKLE CELL DISEASE

TECHNICAL FIELD

The present invention relates to an agent for ameliorating and/or preventing sickle cell disease, and more particularly to an agent for ameliorating and/or preventing sickle cell disease, the agent comprising 5-aminolevulinic acid (5-ALA) or a derivative thereof or a salt thereof, and amelioration and/or prevention of sickle cell disease using the same. Furthermore, the present invention relates to an agent for ameliorating and/or preventing sickle cell disease, the agent comprising 5-ALA or a derivative thereof and a metal-comprising compound, and amelioration and/or prevention of sickle cell disease using the same.

BACKGROUND ART

Sickle cell disease (SCD) is an inherited red blood cell disorder with a single amino acid mutation in which glutamic acid is replaced by valine on the β-chain of hemoglobin S (HbS). By the mutation, negative charge is lost and hydrophobicity is enhanced, whereby dimer and tetramer formations of hemoglobin (Hb) become abnormal, and the polymerization of HbS is induced. When HbS is deoxygenated, the aggregates of HbS form dense polymers, and transform red blood cells into a "sickle" form. This deformation of the red blood cells causes various symptoms occurring in SCD patients, that is, hemolytic anemia, vascular occlusion with pain, organ dysfunction, and shortening of lifespan, and the like (Non Patent Literature 1).

For example, the adherence of sickle cells to white blood cells, platelets, and vascular endothelium causes vascular occlusion in capillary venules to cause hypoxia, thereby ultimately damaging organs. The depletion of free Hb and heme, haptoglobin, and hemopexin scavengers deteriorates pro-inflammatory, pro-adherent, and pro-coagulant environments within the vessel wall. Finally, ischemia reperfusion injury occurs when blood flow is restored, and the production of more reactive oxygen species (ROS) is induced (Non Patent Literature 1).

The sickle cells also increase oxidative stress by inducing the activation of signal transducers. Therefore, the sickle cells not only adhere to the inner wall of the blood vessel, but also induce further vascular occlusion by activating white blood cells and platelets circulating in the body, whereby the white blood cells and platelets adhering to the inner wall of the blood vessel trap the sickle cells. The adhesion of the sickle cells to the inner wall of the blood vessel induces the expression of hyper-adherent proteins and blood procoagulant proteins on the surface of the inner wall cell of the blood vessel. Chronic platelet activation and aggregation have been observed in the SCD patients (Non Patent Literature 1).

Hem derived from sickle cells activates a Toll-like receptor 4 (TLR4) of an innate immune system, and causes tissue disorders such as oxidant production, inflammatory reactions, vascular occlusion, ischemia, and lung disorders (Non Patent Literature 1).

The various symptoms caused by the sickle cells cause further deoxygenation and polymerization of HbS by causing a decrease in blood flow, cause sickling of red blood cells, stagnation of body fluid flow, release of Hb and free heme, vascular occlusion, and an inflammatory reaction and the like, and cause multiple organ failure and pain in the SCD patients. As described above, various symptoms in SCD are complicatedly related to each other (Non Patent Literature 1).

As of 2015, 4.4 million people are affected with sickle cell disease and additional 400 million people are heterozygous for the trait of the sickle cell disease, namely sickle cell mutation (Non Patent Literatures 2 and 3). 114800 people have died from the sickle cell disease (Non Patent Literature 4).

It has been known that bleeding occurs at a high rate in association with the above symptoms in the SCD patients. It has been known that cerebral bleeding, gastrointestinal bleeding, ocular bleeding, gross hematuria, nasal bleeding, menorrhagia, and other bleeding symptoms occur. It has also been found that bleeding events in the SCD patients are associated with a higher risk of death (Non Patent Literature 5).

The only curative therapy for the sickle cell disease is hematopoietic stem cell transplantation (HSCT) or gene therapy, but both are accessible to a very limited number of patients, whereby various therapeutic agents have been developed to ameliorate and/or prevent the symptoms. For example, hydroxyurea is used as a drug that enhances the expression of HbF by suppressing the polymerization of HbS. However, since the drug efficacy of hydroxyurea is not constant for each cell or patient, careful follow-up is required during use. HDAC inhibitors have also been used for similar purposes, but intermittent administration is required to avoid toxicity. A carbon monoxide drug or the like is used as a drug that suppresses sickling by suppressing deoxygenation of HbS and an increase in Hb concentration. However, the drug that changes the affinity between Hb and oxygen has a concern of side effects on organs having a high oxygen demand, for example, brain and kidney. N-acetylcysteine (NAC) or the like is used as a drug that suppresses ischemia reperfusion in SCD and ROS production associated therewith. The application of a drug that suppresses an inflammatory reaction, which is an important factor in the expansion of tissue damage in SCD, has also been studied. However, these have not yet been approved as therapeutic agents for SCD (Non Patent Literature 1).

Therefore, there is still a need for the development of more effective therapeutic agents for ameliorating or preventing the symptoms of SCD.

CITATION LIST

Non Patent Literature

Non Patent Literature 1: Nature Reviews Drug Discovery, 2019, Vol. 18, No. 2, pp. 139-158

Non Patent Literature 2: Lancet., 2016, Vol. 388, No. 10053, pp. 1545-1602

Non Patent Literature 3: Lancet., 2015, Vol. 386, No. 9995, pp. 743-800

Non Patent Literature 4: Lancet., 2016, Vol. 388, No. 10053, pp. 1459-1544

Non Patent Literature 5: Blood advances., 2020, Vol. 4, No. 5, pp. 793-802

SUMMARY OF INVENTION

Technical Problem

An object of the present invention is to provide a novel agent for ameliorating and/or preventing sickle cell disease. More particularly, it is an object of the present invention to provide an agent for ameliorating and/or preventing sickle cell disease, the agent comprising 5-ALA or a derivative thereof or a salt thereof.

Solution to Problem

As a result of intensive studies to solve the above problems, the present inventors have found that, quite unexpectedly, 5-ALA suppresses an increase in sickle cells in SCD, and particularly significantly suppresses an increase in sickle cells in a hypoxic state, thereby preventing or ameliorating sickle cell disease, and have completed the present invention.

5-ALA is a common precursor of heme-based compounds produced in mitochondria in cells. It has been known that 5-ALA exhibits an anti-inflammatory effect on specific inflammatory diseases, but it has not been known that 5-ALA can directly suppress an increase in sickle cells to ameliorate or prevent the symptoms of SCD.

Accordingly, the present invention newly provides a medicament comprising 5-ALA and use thereof for preventing or ameliorating sickle cell disease.

That is, the present invention provides the following items.

[Item 1]

(1) An agent for ameliorating and/or preventing sickle cell disease, the agent comprising a compound represented by Formula (I) below or a salt thereof:

[Chemical Formula 1]

(I)

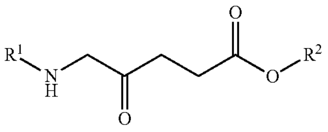

wherein: $R^1$ represents a hydrogen atom or an acyl group; and $R^2$ represents a hydrogen atom, a linear or branched alkyl group, a cycloalkyl group, an aryl group, or an aralkyl group.

[Item 2]

The agent for ameliorating and/or preventing sickle cell disease according to Item 1, wherein $R^1$ and $R^2$ are hydrogen atoms.

[Item 3]

The agent for ameliorating and/or preventing sickle cell disease according to Item 1 or 2, further comprising one or more kinds of metal-comprising compounds.

[Item 4]

The agent for ameliorating and/or preventing sickle cell disease according to Item 3, wherein the metal-comprising compound is a compound comprising iron, magnesium, zinc, nickel, vanadium, copper, chromium, molybdenum, or cobalt.

[Item 5]

The agent for ameliorating and/or preventing sickle cell disease according to Item 3, wherein the metal-comprising compound is a compound comprising iron, magnesium, or zinc.

[Item 6]

The agent for ameliorating and/or preventing sickle cell disease according to Item 3, wherein the metal-comprising compound is a compound comprising iron.

[Item 7]

(1) A method for ameliorating and/or preventing sickle cell disease, the method comprising administering a compound represented by formula (I) below or a salt thereof together with a pharmaceutically acceptable excipient:

[Chemical Formula 2]

(I)

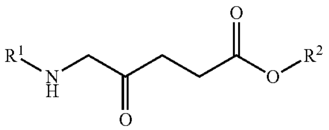

wherein: $R^1$ represents a hydrogen atom or an acyl group; and $R^2$ represents a hydrogen atom, a linear or branched alkyl group, a cycloalkyl group, an aryl group, or an aralkyl group.

Advantageous Effects of Invention

The agent for ameliorating and/or preventing sickle cell disease of the present invention can have an excellent effect of ameliorating/preventing sickle cell disease, and can greatly ameliorate the QOL of patients.

DETAILED DESCRIPTION OF THE PREFERRED EMBODIMENT

Definitions

Figure 1:
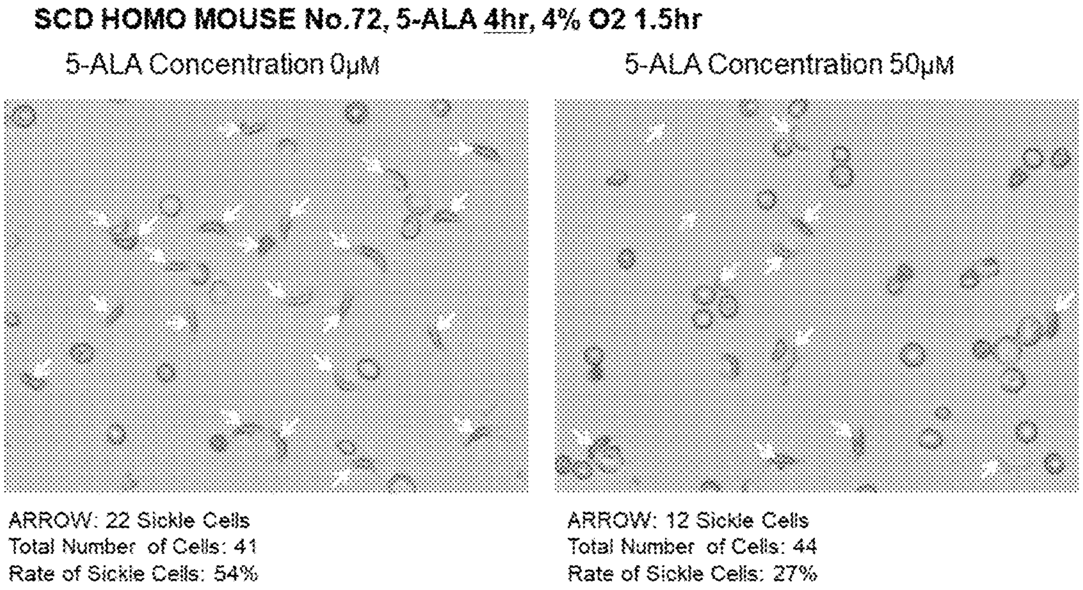
FIG. 1 is a figure showing an optical microscope image of a stained specimen showing an effect of suppressing sickle cells by 5-ALA hydrochloride. Arrows indicate sickle cells.

In the present specification, when a plurality of numerical ranges are indicated, a range consisting of a combination of any lower limit value and upper limit value of the plurality of ranges is also meant as well.

(Active Ingredient of Agent for Ameliorating and/or Preventing Sickle Cell Disease of the Present Invention)

A compound used as an active ingredient of an agent for ameliorating and/or preventing sickle cell disease of the present invention can be exemplified by a compound represented by Formula (I) or a salt thereof (hereinafter, these may be collectively referred to as "ALAS"). 5-ALA, also referred to as 5-aminolevulinic acid, is a type of amino acid in which both $R^1$ and $R^2$ in Formula (I) are hydrogen atoms. Examples of a 5-ALA derivative include compounds other than 5-ALA in which $R^1$ in Formula (I) is a hydrogen atom or an acyl group, and $R^2$ in Formula (I) is a hydrogen atom, a linear or branched alkyl group, a cycloalkyl group, an aryl group, or an aralkyl group.

Examples of the acyl group in Formula (I) include linear or branched alkanoyl groups having 1 to 8 carbon atoms such as formyl, acetyl, propionyl, butyryl, isobutyryl, valeryl, isovaleryl, pivaloyl, hexanoyl, octanoyl, and benzylcarbonyl groups, and aroyl groups having 7 to 14 carbon atoms such as benzoyl, 1-naphthoyl, and 2-naphthoyl groups.

Examples of the alkyl group in Formula (I) include linear or branched alkyl groups having 1 to 8 carbon atoms such as methyl, ethyl, propyl, isopropyl, butyl, isobutyl, sec-butyl, tert-butyl, pentyl, isopentyl, neopentyl, hexyl, heptyl, and octyl groups.

Examples of the cycloalkyl group in Formula (I) include cycloalkyl groups having 3 to 8 carbon atoms in which a saturated or partially unsaturated bond may be present, such as cyclopropyl, cyclobutyl, cyclopentyl, cyclohexyl, cycloheptyl, cyclooctyl, cyclododecyl, and 1-cyclohexenyl groups.

Examples of the aryl group in Formula (I) include aryl groups having 6 to 14 carbon atoms such as phenyl, naphthyl, anthryl, and phenanthryl groups.

As the aralkyl group in Formula (I), an aryl moiety can be exemplified by the same examples as those in the above-mentioned aryl group. An alkyl moiety can be exemplified by the same examples as those in the above-mentioned alkyl group. Specific examples thereof include aralkyl groups having 7 to 15 carbon atoms such as benzyl, phenethyl, phenylpropyl, phenylbutyl, benzhydryl, trityl, naphthylmethyl, and naphthylethyl groups.

The 5-ALA derivative is preferably a compound in which $R^1$ is a formyl, acetyl, propionyl, or butyryl group or the like, and a compound in which $R^2$ is a methyl, ethyl, propyl, butyl, or pentyl group or the like. A compound in which the combination of $R^1$ and $R^2$ is a combination of formyl and methyl, acetyl and methyl, propionyl and methyl, butyryl and methyl, formyl and ethyl, acetyl and ethyl, propionyl and ethyl, or butyryl and ethyl, or the like is preferable.

The 5-ALAs may act as an active ingredient in a state of 5-ALA of Formula (I) or a derivative thereof in vivo, and may be administered as various salts, esters, or prodrugs (precursors) degraded by enzymes in vivo for enhancing solubility, depending on the form to be administered. Examples of salts of 5-ALA and a derivative thereof include pharmacologically acceptable acid addition salts, metal salts, ammonium salts, and organic amine addition salts. Examples of the acid addition salt include inorganic acid salts such as hydrochloride, hydrobromide, hydroiodide, phosphate, nitrate and sulfate; and organic acid addition salts such as formate, acetate, propionate, toluenesulfonate, succinate, oxalate, lactate, tartrate, glycolate, methanesulfonate, butyrate, valerate, citrate, fumarate, maleate, and malate. Examples of the metal salt include alkali metal salts such as a lithium salt, a sodium salt, and a potassium salt, alkaline earth metal salts such as a magnesium salt and a calcium salt, and metal salts of aluminum and zinc and the like. Examples of the ammonium salt include alkylammonium salts such as an ammonium salt and a tetramethylammonium salt. Examples of the organic amine salt include salts such as a triethylamine salt, a piperidine salt, a morpholine salt, and a toluidine salt. These salts can also be used as solutions at the time of use.

Among the above ALAs, desirable are 5-ALA and various esters such as

5-ALA methyl ester, 5-ALA ethyl ester, 5-ALA propyl ester, 5-ALA butyl ester, and 5-ALA pentyl ester, as well as hydrochloride, phosphate, and sulfate salts thereof. ALA hydrochloride and 5-ALA phosphate can be particularly suitably exemplified.

The ALAs can be produced by any known method such as chemical synthesis, microorganic production, or enzymatic production. The ALAs may also form a hydrate or a solvate. Any of them can be used alone or in an appropriate combination of two or more thereof.

The agent for ameliorating and/or preventing sickle cell disease of the present invention preferably further comprises a metal-comprising compound as long as excess disease does not occur. Examples of the metal moiety of the metal-comprising compound include iron, magnesium, zinc, nickel, vanadium, cobalt, copper, chromium, and molybdenum, but iron, magnesium, and zinc are preferable, and among them, iron can be suitably exemplified.

The ALAs and the metal-comprising compound are used in combination, whereby an excellent effect of ameliorating and/or preventing sickle cell disease can be obtained even when ALAs having a lower concentration are used.

The iron compound may be an organic salt or an inorganic salt. Examples of the inorganic salt include ferric chloride, iron sesquioxide, iron sulfate, and ferrous pyrophosphate. Examples of the organic salt include carboxylates, for example, citrates such as ferrous citrate, sodium iron citrate, sodium ferrous citrate (SFC), and ammonium iron citrate, organic salts such as ferric pyrophosphate, heme iron, dextran iron, iron lactate, ferrous gluconate, sodium diethylenetriamine pentaacetate, ammonium iron diethylenetriamine pentaacetate, sodium iron ethylenediamine tetraacetate, ammonium iron ethylenediaminepentaacetate, sodium iron dicarboxymethylglutamate, ammonium iron dicarboxymethylglutamate, ferrous fumarate, iron acetate, iron oxalate, ferrous succinate, and sodium iron citrate, which are hydroxycarboxylates, and triethylenetetraamine iron, lactoferrin iron, transferrin iron, iron chlorophyllin sodium, ferritin iron, saccharated iron oxide, and glycine ferrous sulfate.

Examples of the magnesium compound include magnesium citrate, magnesium benzoate, magnesium acetate, magnesium oxide, magnesium chloride, magnesium hydroxide, magnesium carbonate, magnesium sulfate, magnesium silicate, magnesium nitrate, magnesium diethylenetriaminepentaacetate diammonium, magnesium ethylenediaminetetraacetate disodium, and magnesium protoporphyrin.

Examples of the zinc compound include zinc chloride, zinc oxide, zinc nitrate, zinc carbonate, zinc sulfate, diammonium zinc diethylenetriaminepentaacetate, disodium zinc ethylenediaminetetraacetate, zinc protoporphyrin, and zinc-comprising yeast.

One or two or more kinds of the metal-comprising compounds can be used, and the dose of the metal-comprising compound may be 0 to 100 times, is desirably 0.01 times to 10 times, and more desirably 0.1 times to 8 times the dose of 5-ALA in terms of molar ratio.

(Method for Administering and/or Preventing Agent of the Present Invention)

The ALAs and the metal-comprising compound comprised in the agent for ameliorating and/or preventing sickle cell disease of the present invention can also be administered as a composition comprising the ALAs and the metal-comprising compound, or as a composition comprising each of the ALAs and the metal-comprising compound alone. When the composition comprising the ALAs alone and the composition comprising the metal-comprising compound alone are used, they may be administered simultaneously or may be administered separately. Preferably, the ALAs and the metal-comprising compound can be administered in combination so that the administration thereof can exhibit an additive effect, preferably a synergistic effect. When the composition comprising the ALAs alone and the composition comprising the metal-comprising compound alone are separately administered, the administration interval thereof can be set to 5 minutes, 10 minutes, 15 minutes, 20 minutes, 30 minutes, 45 minutes, 1 hour, 2 hours, 3 hours, 4 hours, 5 hours, 6 hours, 7 hours, 8 hours, 9 hours, 10 hours, 11 hours, and 12 hours and the like, but is not limited thereto.

Examples of the administration route of the agent for ameliorating and/or preventing sickle cell disease of the present invention include oral administration including sublingual administration, or parenteral administration such as intravenous administration by inhalation administration, injection, or drip infusion or the like, transdermal administration by cataplasm, gel, or lotion or the like, suppository, or administration by forced enteral nutrition using a nasogastric tube, a nasoenteral tube, a gastric fistula tube, or an intestinal fistula tube.

(Dosage Form of Ameliorating and/or Preventing Agent of the Present Invention)

The dosage form of the agent for ameliorating and/or preventing sickle cell disease of the present invention can be appropriately determined according to the administration routes, and examples thereof include injections, drop infusions, tablets, capsules, fine granules, powders, solutions, liquors dissolved in syrups or the like, poultices, and suppositories.

In order to prepare the agent for ameliorating and/or preventing sickle cell disease of the present invention, a pharmacologically acceptable carrier, an excipient, a diluent, an additive, a disintegrant, a binder, a covering agent, a lubricant, a gliding agent, a lubricating agent, a flavoring agent, a sweetening agent, a solubilizing agent, a solvent, a gelling agent, and a nutrient and the like can be added as necessary, and a person skilled in the art can select each specific component according to the purpose. When the agent for ameliorating and/or preventing sickle cell disease of the present invention is prepared as an aqueous solution, it is necessary to pay attention so that the aqueous solution does not become alkaline in order to prevent the decomposition of ALAs. When the aqueous solution becomes alkaline, the decomposition can be prevented by removing oxygen.

(Dosage Amount of Ameliorating and/or Preventing Agent of the Present Invention)

The amount, frequency, and period of administration of the agent for ameliorating and/or preventing sickle cell disease of the present invention vary depending on the age, weight, and symptoms and the like of a patient with sickle cell disease or a person trying to prevent sickle cell disease, but the dose of ALAs can be 0.01 mmol to 25 mmol/day, preferably 0.025 mmol to 7.5 mmol/day, more preferably 0.075 mmol to 5.5 mmol/day, and still more preferably 0.2 mmol to 2 mmol/day per adult on a 5-ALA molar basis. In particular, when the agent is used as a preventing agent, it is desirable to continuously ingest a low dosage. Examples of the administration frequency can include one to a plurality of administrations per day or continuous administration by drip infusion or the like. The period of administration as an ameliorating agent or preventing agent can be determined according to known methods by pharmacologists and clinicians in the art based on indicators indicative of the condition of sickle cell disease.

Hereinafter, the present invention will be described in more detail with reference to Examples, but the present invention is not limited by these Examples.

Example 1

Culture of Red Blood Cells Collected from SCD Model Mice

SCD model mice aged 8 to 20 weeks were used. In the mice, a human HBA gene and a human HBB gene are knocked in a mouse HBA gene locus and a mouse HBB gene locus, respectively, and a gene mutation ($\beta^s$ mutation) causing amino acid substitution (Val6Glu) causing SCD is introduced into the human HBB gene. Furthermore, a human HBG gene is introduced, and expression switching from post-natal γ-globin to β-globin is designed to occur as in humans. Therefore, an SCD model mouse homozygously carrying the $\beta^s$ mutation (SCD homo mouse) exhibits symptoms similar to those of human SCD. The SCD homo mouse was anesthetized with isoflurane, and 100 μl of blood was then collected from the vein behind the jawbone into an EDTA-2Na-coated blood sampling tube using an animal lamp set. The coagulation of the blood was prevented by lightly tapping the tube. The collected blood was transferred to a 1.5 ml tube, and centrifuged for 10 minutes under conditions of 3000 rpm and 4° C. After removing the supernatant, 1 ml of PBS was added to the precipitated red blood cells, followed by mixing by inversion, to wash the cells. The red blood cells obtained by repeating this washing operation again were diluted 200 times with a cell culture solution (RPMI 1640, 10% FBS, 1% Penicillin-Streptomycin-Fungizone Cocktail), and cultured under the conditions of 37° C., 5% $CO_2$, and 21% $O_2$. This red blood cell culture solution was used in the experiment within 5 days from the start of culture.

Example 2

Effect of 5-ALA Hydrochloride on Sickling by Hypoxia Exposure of Red Blood Cells Collected from SCD Homo Mice and Cultured 5-ALA hydrochloride was added to the red blood cell culture solution of Example 1 so as to be 0, 10, 25, and 50 μM, and the red blood cells were cultured under the conditions of 37° C., 5% $CO_2$, and 21% $O_2$ for 4 hours. Thereafter, the red blood cells were cultured under the conditions of 37° C., 5% $CO_2$, and 4% $O_2$ for 1.5 hours to induce the sickling of the red blood cells. After the completion of the culture, paraformaldehyde was added so as to have a final concentration of 2%, and the mixture was allowed to stand for 10 minutes under the conditions of 37° C., 5% $CO_2$, and 4% $O_2$ to fix the red blood cells. 50 ml of the fixed red blood cell culture solution was centrifuged at 500 rpm for 6 minutes using a cell collecting centrifuge to prepare a smear specimen. The smear specimen was immersed in a Megruenwald stain solution for 5 minutes, and then immersed in a Giemsa stain solution for 25 minutes. Then, the excess stain solution was washed with tap water, and the smear specimen was dried with cold air using a dryer to prepare a May-Giemsa stained specimen. The May-Giemsa stained specimen was observed at 600 fold using an optical microscope, and the number of sickled red blood cells was measured. The sickling rates of the groups were compared with each other to examine the effect of 5-ALA hydrochloride on cultured red blood cell sickling by hypoxic exposure.

As a result, a remarkable decrease in the number of red blood cells showing a sickle form was observed by 5-ALA hydrochloride treatment. FIG. 1 illustrates an optical microscopic image of a stained specimen obtained from a sample obtained by treating red blood cells collected from the same SCD homo mouse (No. 72) with 5-ALA hydrochloride having a concentration of 0 μM (negative control, left panel) or 50 μM (right panel) for 4 hours. Arrows indicate sickle cells. A remarkable decrease in red blood cells exhibiting a sickle form was observed in the samples treated with 5-ALA hydrochloride having a concentration of 50 μM (FIG. 1).

Figure 2:
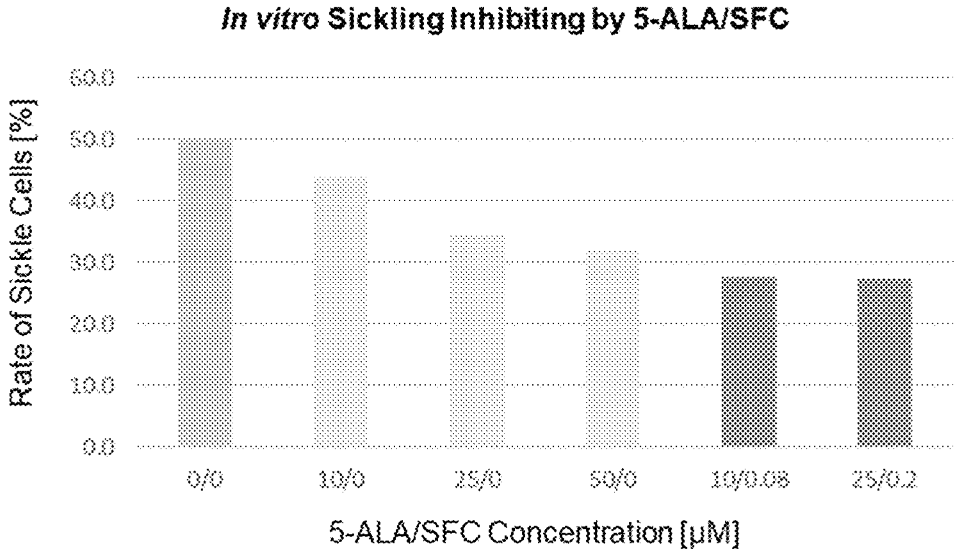
FIG. 2 is a graph showing an effect of suppressing sickle cells using 5-ALA hydrochloride, or using 5-ALA hydrochloride in combination with sodium ferrous citrate (SFC).

As a result of calculating the sickling rates of the groups obtained by measuring the number of sickled red blood cells, a concentration-dependent decrease in the sickling rates was observed by treatment with 5-ALA hydrochlorides of 10, 25, and 50 μM, respectively, as compared with the samples not treated with 5-ALA hydrochloride (0 μM). Sickling rate data obtained from the sample collected from the SCD homo mouse (No. 72) shown in FIG. 1 is shown in FIG. 2. SFC represents sodium ferrous citrate, but treatment with 5-ALA hydrochloride alone resulted in a concentration-dependent decrease in the sickling rate (FIG. 2).

Example 3

Effect of Combination of 5-ALA Hydrochloride and Sodium Ferrous Citrate (SFC) on Sickling by Hypoxia Exposure of Red Blood Cells Collected from SCD Homo Mice and Cultured 5-ALA hydrochloride/SFC was added to the red blood cell culture solution of Example 1 so as to be 10/0.08 and 25/0.2 μM, and red blood cells were cultured under the conditions of 37° C., 5% $CO_2$, and 21% $O_2$ for 4 hours. Thereafter, the red blood cells were cultured under the conditions of 37° C., 5% $CO_2$, and 4% $O_2$ for 1.5 hours to induce the sickling of the red blood cells. After the completion of the culture, red blood cell fixation, May-Giemsa staining, and measurement of the number of sickle cells were performed in the same manner as in Example 2. The sickling rates of the groups were compared with each other to examine the effect of the combination of 5-ALA hydrochloride and SFC on cultured red blood cell sickling by hypoxic exposure.

As a result, it was observed that by using 5-ALA hydrochloride in combination with SFC, an excellent effect of inhibiting sickling can be obtained by the treatment with 5-ALA hydrochloride having a lower concentration. FIG. 2 shows an effect when 5-ALA hydrochloride and SFC are used in combination for the sample collected from the SCD homo mouse (No. 72) shown in FIG. 1. It is shown that when 0.16 μM and 0.4 μM of SFC are used in combination with 10 μM and 25 μM of 5-ALA hydrochloride, respectively, remarkable enhancement of the effect of inhibiting sickling is obtained.

Example 4

Effect of Combination of 5-ALA Hydrochloride and SFC on Number of Blood Cells and Hemoglobin Value of SCD Homo Mice (In Vivo Administration Test)

Figure 3:
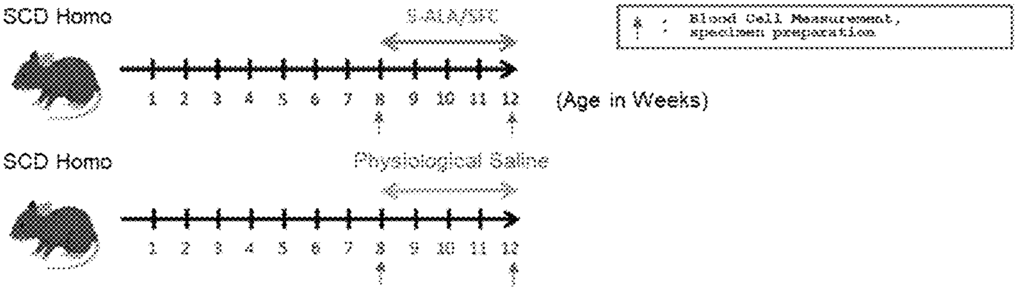
FIG. 3 is a figure showing the outline of an experiment for investigating an effect (in vivo administration test) of a combination of 5-ALA hydrochloride and SFC on the number of red blood cells and hemoglobin value of SCD homo mice.

30 μl of blood was collected from an SCD homo mouse aged 8 weeks in the same manner as in Example 1, and the number of red blood cells and a hemoglobin value were measured using an automated blood cell counter. After blood sampling, 5-ALA hydrochloride/SFC (200/31.4 mg/kg/day) or physiological saline (10 μl/g/day) was administered for 4 weeks. After the completion of the administration, 30 μl of blood was collected in the same manner as in Example 1, and the number of red blood cells and a hemoglobin value were measured using an automated blood cell counter. The measured values before and after the administration of each group were compared with each other, and the effect of the combined administration of 5-ALA hydrochloride and SFC on the number of red blood cells and hemoglobin value of the SCD homo mouse was examined. The outline of the experiment is illustrated in FIG. 3.

Figure 4:
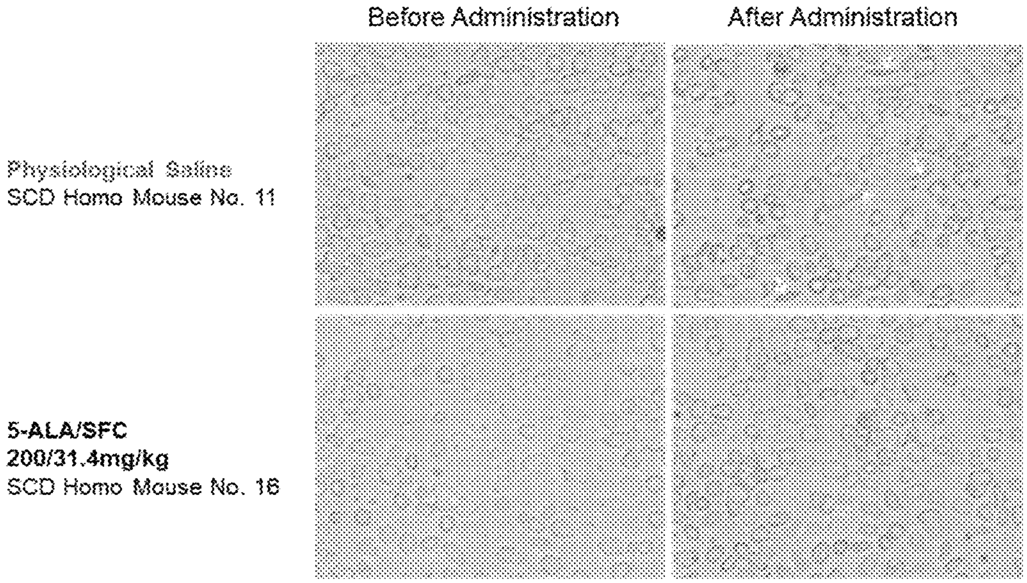
FIG. 4 is a figure showing an optical microscopic image of a stained specimen showing an effect of suppressing sickle cells by the combined in vivo administration of 5-ALA hydrochloride and SFC combined. Arrows indicate sickle cells.
Figure 5:
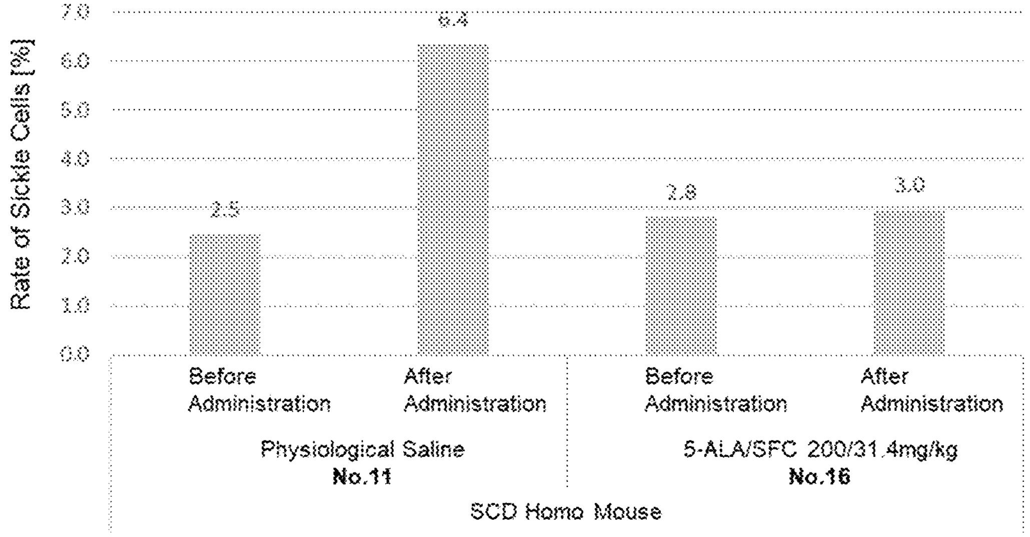
FIG. 5 is a graph showing an effect of suppressing sickle cells by the combined in vivo administration of 5-ALA hydrochloride and SFC combined.

As a result of the experiment, by concurrently administering 5-ALA hydrochloride and SFC for 4 weeks, a decrease in the number of red blood cells and the hemoglobin value in the SCD homo mouse was suppressed. Conversely, as an increase in these values was observed, an increase in the ratio of sickle cells was suppressed. The optical microscopic image of a stained specimen is shown in FIG. 4. Arrows indicate sickle cells. Changes in the number of red blood cells and the hemoglobin value are shown in Table 1 below, and changes in the rates of the sickle cells are shown in FIG. 5.

TABLE 1

| Group (n = 1 each) | | Number of Red Blood Cells [×$10^6$ Cells/ml] | Hemoglobin Value [g/dl] |
|---|---|---|---|
| Physiological Saline | Before Administration | 7.78 | 8.3 |
| | After Administration | 7.02 | 7.2 |
| 5-ALA/SFC 200/31.4 mg/kg | Before Administration | 7.18 | 7.4 |
| | After Administration | 8.72 | 9 |

Example 5

Figure 6:
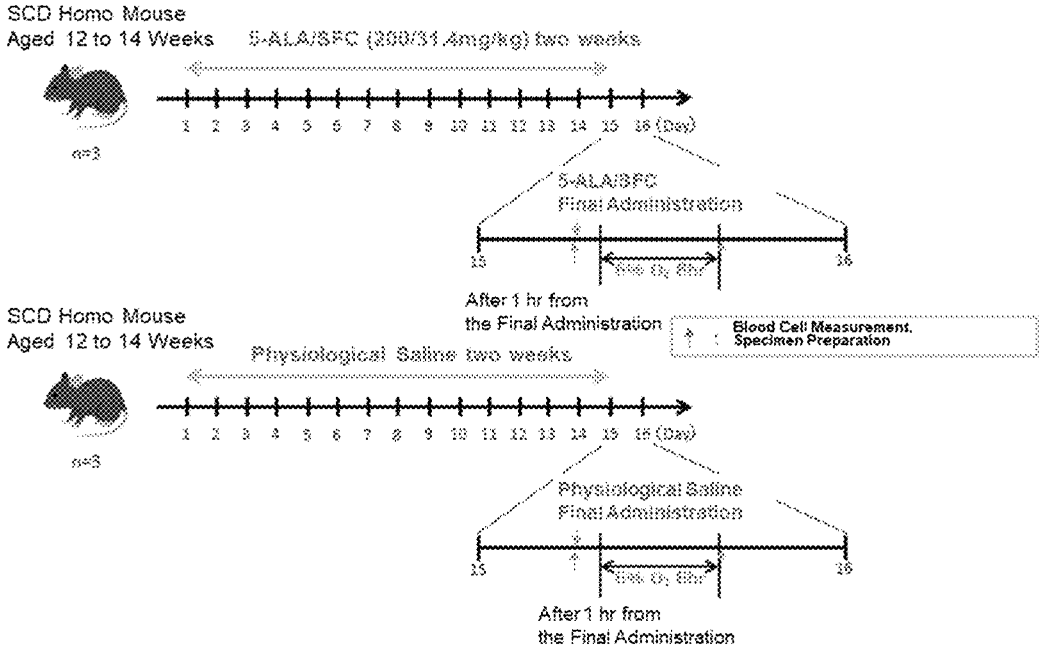
FIG. 6 is a figure showing the outline of an experiment for investigating an effect of a combination of 5-ALA hydrochloride and SFC on red blood cell sickling in vivo caused by hypoxia exposure in SCD homo mice.

Effect of Combination of 5-ALA Hydrochloride and SFC on In Vivo Red Blood Cell Sickling by Hypoxia Exposure in SCD Homo Mice 5-ALA hydrochloride/SFC (200/31.4 mg/kg/day) or physiological saline (10 μl/g/day) was administered to SCD homo mice aged 8 to 12 weeks for 15 days. Immediately before the final administration, 30 μl of blood was collected in the same manner as in Example 1 to prepare a blood smear specimen. After one hour from the final administration, each SCD homo mouse was exposed to 6% $O_2$ for 8 hours. Immediately before the final administration, 30 μl of blood was collected in the same manner as in Example 1 to prepare blood smear specimens. All the prepared smear specimens were stained with May-Giemsa in the same manner as in Example 2, and the number of sickled red blood cells was measured. The sickling rates of the groups before and after hypoxic exposure were compared with each other to examine the effect of the combination of 5-ALA hydrochloride and SFC on red blood cell sickling in vivo by hypoxic exposure. The outline of the experiment is illustrated in FIG. 6.

Figure 7:
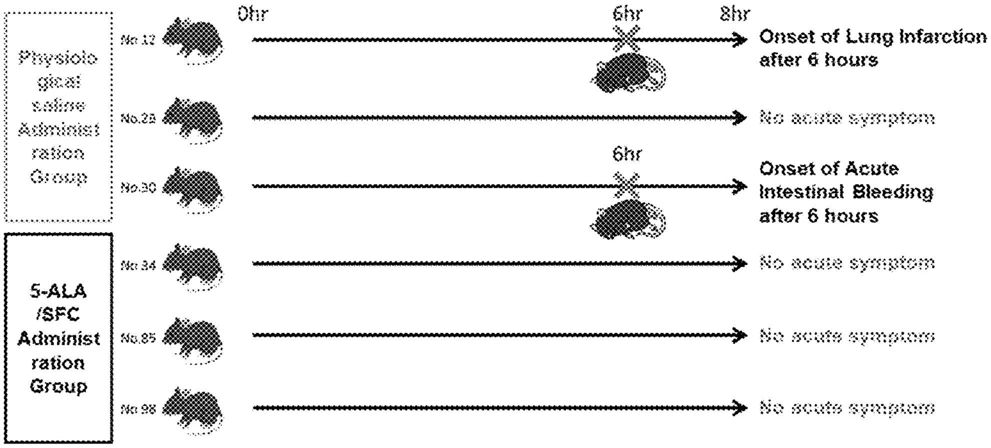
FIG. 7 is a figure showing that hypoxia-induced acute symptoms are suppressed by the combined administration of 5-ALA hydrochloride and SFC.
Figure 8:
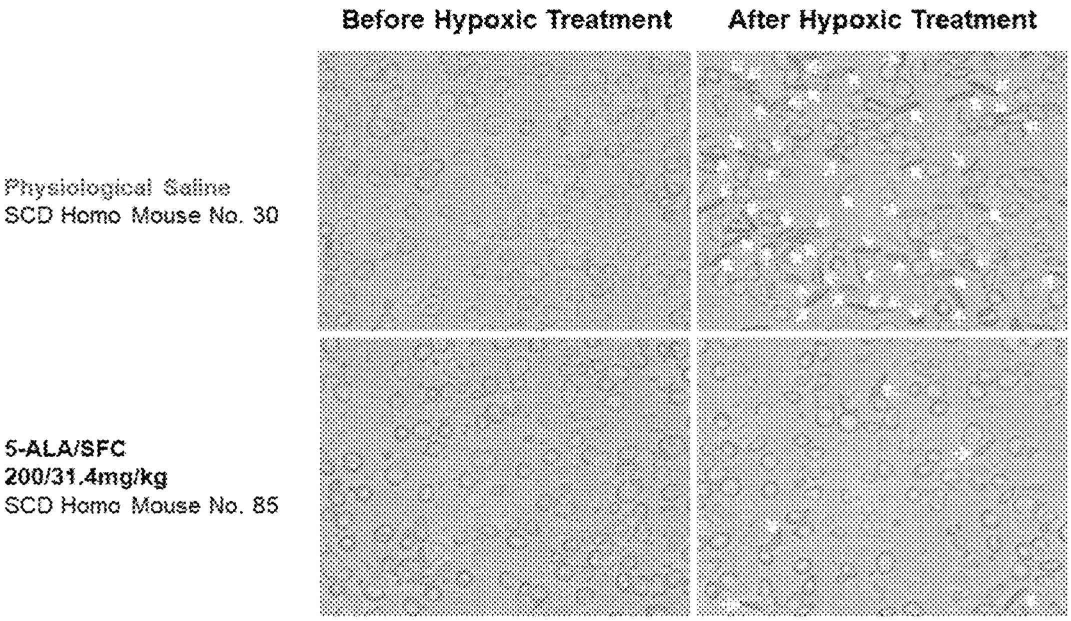
FIG. 8 is a figure showing an optical microscope image of a stained specimen showing that an increase in sickle cells caused by hypoxic induction is suppressed by the combined administration of 5-ALA hydrochloride and SFC. Arrows indicate sickle cells.
Figure 9:
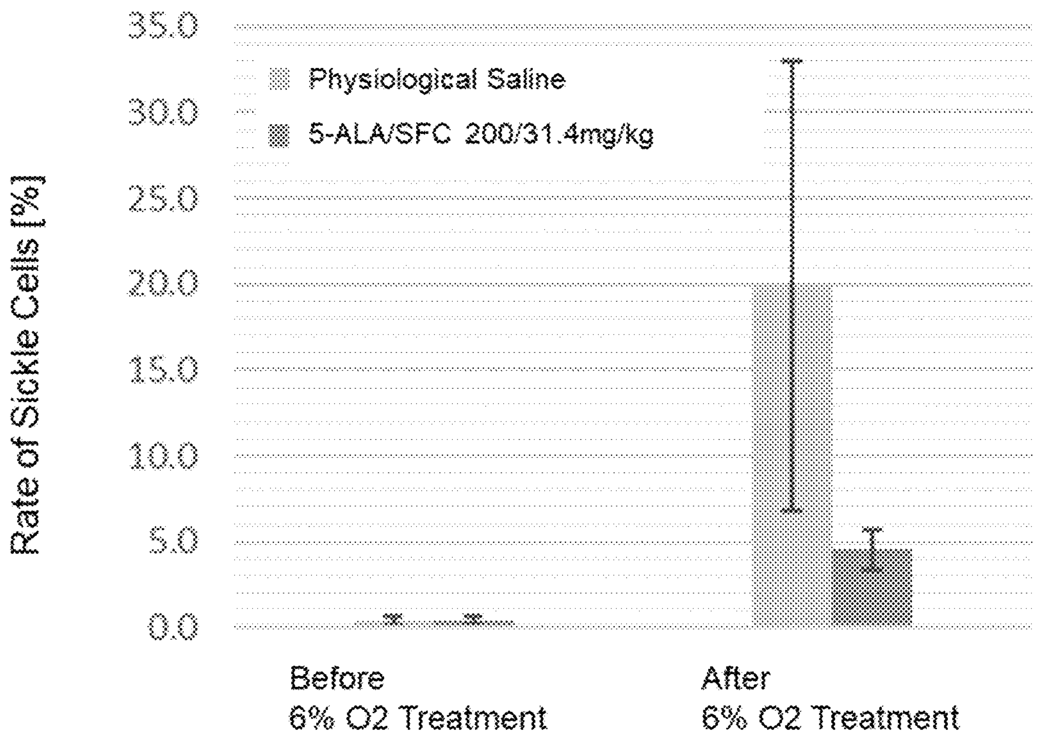
FIG. 9 is a graph showing that an increase in sickle cells caused by hypoxic induction is suppressed by the combined administration of 5-ALA hydrochloride and SFC.

As a result of the experiment, it was observed that by concurrently administering 5-ALA hydrochloride and SFC for 15 days, an increase in sickle cells when the SCD homo mice are subjected to hypoxia-induced treatment is significantly suppressed, and hypoxia-induced acute symptoms are suppressed. As shown in FIG. 7, in the physiological saline administration group, two of three SCD homo mice (Nos. 12 and 30) developed hypoxia-induced acute symptoms such as lung infarction and acute intestinal bleeding within 8 hours after induction of hypoxia, whereas in the group to which 5-ALA hydrochloride and SFC were administered, none of the SCD homo mice developed hypoxia-induced acute symptoms. From the light microscopic images of stained specimens from the SCD homo mice, it was observed that a significant increase in sickle cells after hypoxia induction in the SCD homo mice to which physiological saline is administered is remarkably suppressed by the combined administration of 5-ALA hydrochloride and SFC. FIG. 8 illustrates the optical microscopic images of stained specimens obtained from the SCD homo mouse No. 30 to which physiological saline is administered and the SCD homo mouse No. 85 to which 5-ALA hydrochloride and SFC are concomitantly administered. Arrows indicate sickle cells. The change in the rate of the sickle cells of each SCD homo mouse obtained from the stained specimen is shown in the following Table 2 and FIG. 9.

TABLE 2

| | | Mouse No. | Rate of Sickle Cells (%) | Average (%) |
|---|---|---|---|---|
| Physiological Saline | Before Hypoxic Treatment | 12 | 0 | 0.4 |
| | | 28 | 0.6 | |
| | | 30 | 0.5 | |
| | After Hypoxic Treatment | 12 | 16.8 | 19.9 |
| | | 28 | 5.6 | |
| | | 30 | 37.3 | |
| 5-ALA/SFC 200/31.4 mg/kg | Before Hypoxic Treatment | 34 | 0.4 | 0.4 |
| | | 85 | 0.2 | |
| | | 98 | 0.7 | |
| | After Hypoxic Treatment | 34 | 3 | 4.5 |
| | | 85 | 5.8 | |
| | | 98 | 4.8 | |

As shown in Table 2, in Nos. 12 and 30, the rate of the sickle cells significantly increased. It was found that the combined administration of 5-ALA hydrochloride and SFC suppresses red blood cell sickling due to a hypoxic state to effectively suppress hypoxia-induced acute symptoms.

Example 6

Effect of Combination of 5-ALA Hydrochloride and SFC on Number of Sickle Cells in Blood in SCD Homo Mice at Normal Oxygen Concentration The effect of 5-ALA hydrochloride and SFC on the number of sickle cells in blood at normal oxygen concentration was tested using SCD homo mice.

To SCD homo mice aged 10 to 16 weeks, 5-ALA hydrochloride/SFC (50/3.9 mg/kg/day), 5-ALA hydrochloride (50 mg/kg/day), SFC (3.9 mg/kg/day), or physiological saline (10 μl/g/day) was administered for 4 weeks. On the next day of the final administration, 30 μl of blood was collected in the same manner as in Example 1 to prepare a blood smear specimen. All the prepared smear specimens were stained with May-Giemsa in the same manner as in Example 2, and the ratio of sickle cells to all red blood cells was measured. The rate of the sickle cells of the groups were compared with each other to examine the effect of the combination of 5-ALA hydrochloride and SFC on the rate of the in vivo sickle cells.

Figure 10:
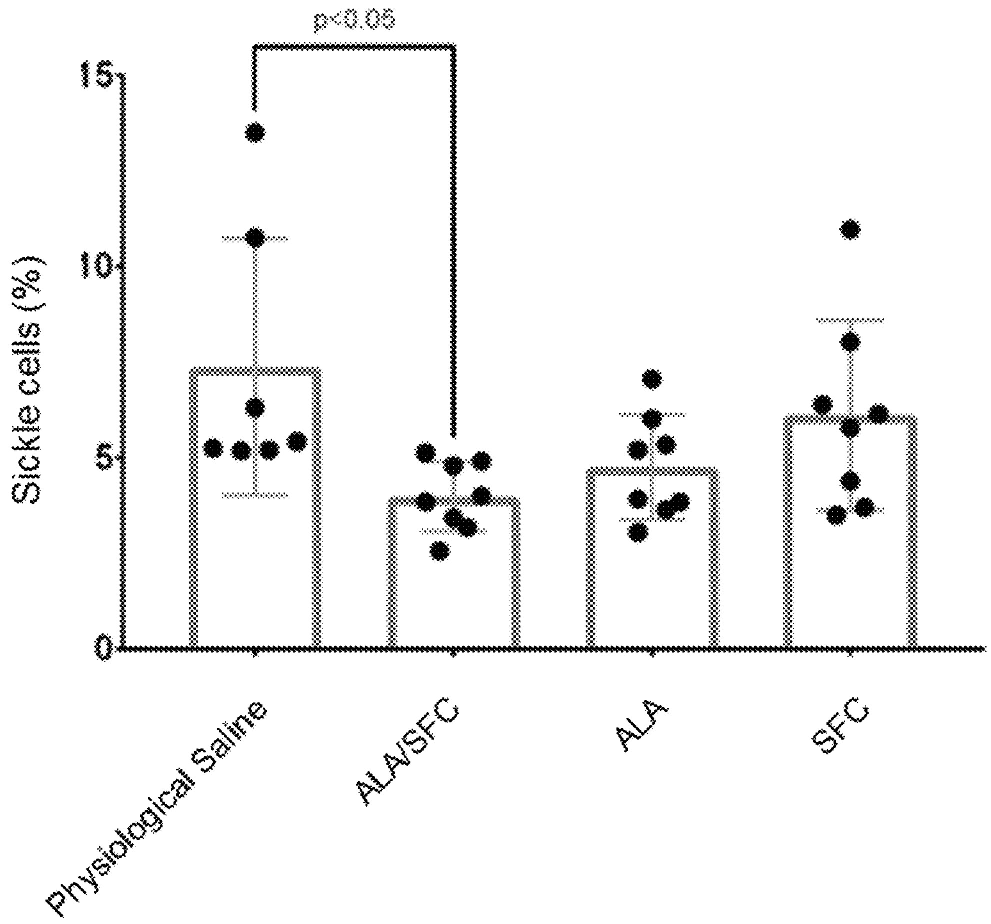
FIG. 10 is a graph showing that the combined administration of 5-ALA hydrochloride and SFC reduces sickle cells in a normal oxygen concentration state in SCD mice.
Figure 11:
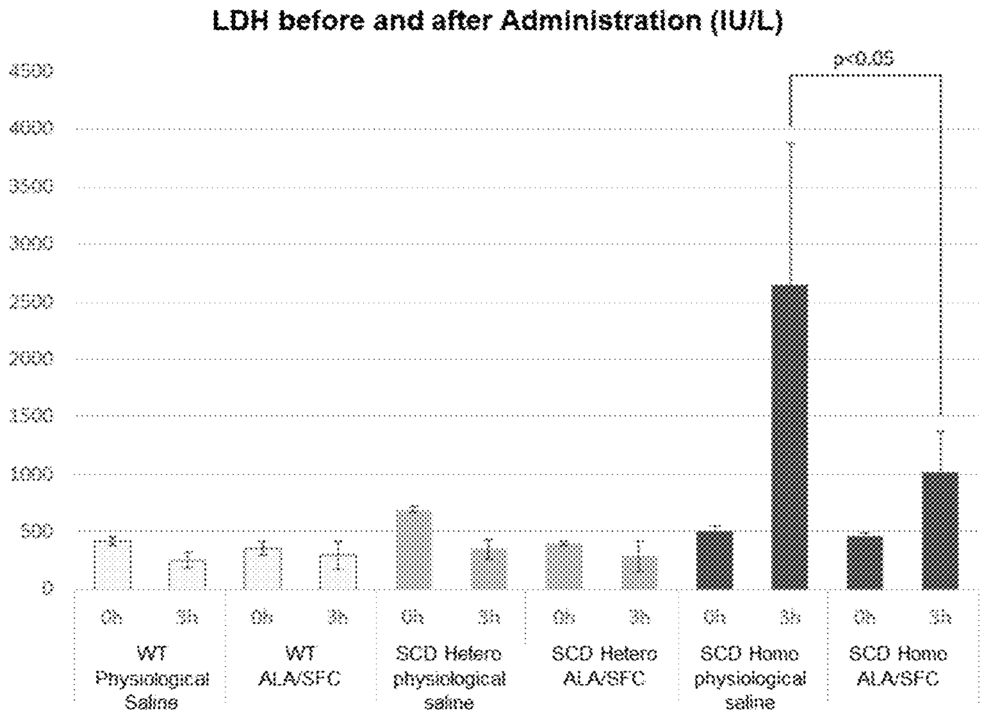
FIG. 11 is a graph showing that the administration of 5-ALA hydrochloride suppresses an increase in blood LDH level in SCD homo mice due to bleeding stress caused by blood sampling.

As a result of the experiment, it was confirmed that the rate of the in vivo sickle cells slightly decreases in the group to which 5-ALA hydrochloride is administered, as compared with the group to which physiological saline is administered. There was little effect on the rate of the in vivo sickle cells in the group to which SFC alone was administered. Meanwhile, in the group to which 5-ALA hydrochloride and SFC were concomitantly administered, a significant decrease in the rate of the in vivo sickle cells was observed, and a statistically significant ($P<0.05$) effect of decreasing the rate of the sickle cells was confirmed as compared with the group to which physiological saline was administered (FIG. 10).

Example 7

Effect of 5-ALA Hydrochloride on Bleeding Stress Due to Blood Sampling in SCD Model Mice Lactate dehydrogenase (LDH) is one of main enzymes of an anaerobic glycolytic system in a cytoplasm, and its blood concentration is used as a marker of tissue damage. It is known that LDH levels in blood increase in SCD patients in association with intravascular hemolysis, damage due to ischemia reperfusion, and tissue necrosis and the like. It is known that in the SCD patients, the LDH levels may increase chronically, and the LDH levels markedly increase at the time of the acute onset of vascular occlusion or the like. Intravascular hemolysis in the SCD patients also causes elevated LDH levels in blood (Clinica Chimica Acta, 2016, vol. 458, pp. 99-102). Using the LDH levels in blood in the SCD model mice as an index, the effect of 5-ALA hydrochloride on bleeding stress due to blood sampling in the SCD patients was examined.

Immediately after 200 μl of blood was collected from SCD model mice aged 9 weeks in the same manner as in Example 1, 5-ALA hydrochloride/SFC (50/3.9 mg/kg) or physiological saline (10 μl/g) was administered. After 3 hours from the administration, 50 μl of blood was collected again in the same manner as in Example 1. The LDH levels in the blood collected before and after the administration were measured, and the effect of the combination of 5-ALA hydrochloride and SFC on bleeding stress due to blood sampling was evaluated.

As a result of the experiment, in the wild-type mouse and the SCD hetero mouse to which physiological saline was administered, when the level of LDH in blood (blood sampling 1) obtained by first blood sampling was compared with the level of LDH in blood (blood sampling 2) obtained by blood sampling after 3 hours from the first blood sampling, the blood sampling 2 had a slightly lower LDH level. Meanwhile, in the SCD homo mouse to which physiological saline was administered, a marked increase in the LDH level was confirmed in the blood sampling 2. The marked increase in the LDH level was markedly suppressed by the administration of 5-ALA hydrochloride, particularly 5-ALA hydrochloride/SFC (50/3.9 mg/kg) (FIG. 10).

The present experiment revealed that the administration of 5-ALA hydrochloride suppresses bleeding stress due to acute blood sampling in the SCD patients. It is considered that acute onset of vascular occlusion and tissue damage due to intravascular hemolysis or bleeding stress in the SCD patients are suppressed by the administration of 5-ALA hydrochloride, particularly 5-ALA hydrochloride/SFC.

What is claimed is:

1. A method for ameliorating sickle cell disease, comprising:

administering an agent to a subject having hemoglobin S or $\beta^S$ mutation on HBB gene or showing a symptom of sickle cell disease in an amount effective for ameliorating the symptoms of sickle cell disease or effective to suppress onset of a symptom of sickle cell disease, the agent comprising a compound represented by Formula (I) below or a salt thereof:

(I)

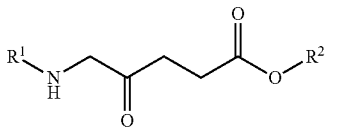

wherein: $R^1$ represents a hydrogen atom or an acyl group; and $R^2$ represents a hydrogen atom, a linear or branched alkyl group, a cycloalkyl group, an aryl group, or an aralkyl group.

2. The method for ameliorating sickle cell disease according to claim 1, wherein $R^1$ and $R^2$ are hydrogen atoms.

3. The method for ameliorating sickle cell disease according to claim 1, the agent further comprising one or more kinds of metal-comprising compounds.

4. The method for ameliorating sickle cell disease according to claim 3, wherein the metal-comprising compound is a compound comprising iron, magnesium, zinc, nickel, vanadium, copper, chromium, molybdenum, or cobalt.

5. The method for ameliorating sickle cell disease according to claim 3, wherein the metal-comprising compound is a compound comprising iron, magnesium, or zinc.

6. The method for ameliorating sickle cell disease according to claim 3, wherein the metal-comprising compound is a compound comprising iron.

7. The method for ameliorating sickle cell disease according to claim 1, wherein said agent is administered to said subject in an amount effective to decrease the number of red blood cells showing a sickle form.

8. The method for ameliorating sickle cell disease according to claim 1, wherein said agent is administered to said subject in an amount effective to decrease the sickling rate of red blood cells in said subject.

9. The method for ameliorating sickle cell disease according to claim 1, wherein said agent is administered as a salt of said compound represented by Formula (I).

10. The method for ameliorating sickle cell disease according to claim 9, wherein said salt is a hydrochloride salt or a phosphate salt.

11. The method for ameliorating sickle cell disease according to claim 9, wherein said salt is a hydrochloride salt.

12. The method for ameliorating sickle cell disease according to claim 9, wherein a hydrochloride salt of the compound represented by Formula (I) and sodium ferrous citrate (SFC) are administered in combination and the combined administration suppresses red blood cell sickling due to a hypoxic state to suppress hypoxia-induced acute symptoms.

13. The method for ameliorating sickle cell disease according to claim 1, wherein said subject has one of said mutations.

14. The method for ameliorating sickle cell disease according to claim 6, wherein a hydrochloride salt of the compound represented by Formula (I) and sodium ferrous citrate (SFC) are administered in combination and the combined administration suppresses red blood cell sickling due to a hypoxic state to suppress hypoxia-induced acute symptoms.

15. A method for ameliorating sickle cell disease, comprising:

administering an agent to a subject having sickle cell disease in an amount effective for ameliorating the symptoms of sickle cell disease or effective to suppress onset of a symptom of said sickle cell disease, the agent comprising a compound represented by Formula (I) below or a salt thereof:

(I)

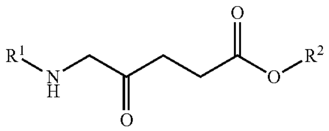

wherein: $R^1$ represents a hydrogen atom or an acyl group; and $R^2$ represents a hydrogen atom, a linear or branched alkyl group, a cycloalkyl group, an aryl group, or an aralkyl group.

* * * * *